US009955952B2

(12) United States Patent
Hirama et al.

(10) Patent No.: US 9,955,952 B2
(45) Date of Patent: May 1, 2018

(54) ULTRASONIC DIAGNOSTIC DEVICE AND CORRECTION METHOD

(71) Applicant: Toshiba Medical Systems Corporation, Otawara-shi (JP)

(72) Inventors: Makoto Hirama, Otawara (JP); Yasuhiko Abe, Otawara (JP); Takeshi Sato, Nasushiobara (JP); Yasunori Honjo, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 203 days.

(21) Appl. No.: 14/713,147

(22) Filed: May 15, 2015

(65) Prior Publication Data

US 2015/0327840 A1    Nov. 19, 2015

(30) Foreign Application Priority Data

May 19, 2014  (JP) ................................ 2014-103715

(51) Int. Cl.
| | |
|---|---|
| *A61B 8/08* | (2006.01) |
| *A61B 8/00* | (2006.01) |
| *A61B 8/14* | (2006.01) |
| *G01S 7/52* | (2006.01) |
| *G01S 15/89* | (2006.01) |

(52) U.S. Cl.
CPC ........... *A61B 8/5253* (2013.01); *A61B 8/463* (2013.01); *A61B 8/5207* (2013.01); *A61B 8/5269* (2013.01); *G01S 7/52049* (2013.01); *G01S 15/8995* (2013.01); *A61B 8/08* (2013.01)

(58) Field of Classification Search
None
See application file for complete search history.

(56) References Cited

U.S. PATENT DOCUMENTS 6,699,189 B1 * 3/2004 Lin ...................... A61B 8/0875
                                                         600/437

FOREIGN PATENT DOCUMENTS

| JP | 2009-219876 | 10/2009 |
|---|---|---|
| JP | 2009-254462 | 11/2009 |
| JP | 2011-120765 | 6/2011 |

* cited by examiner

*Primary Examiner* — Katherine Fernandez
*Assistant Examiner* — Bradley Impink
(74) *Attorney, Agent, or Firm* — Oblon, McClelland, Maier & Neustadt, L.L.P.

(57) ABSTRACT

An ultrasonic diagnostic device includes transmission circuitry, reception circuitry, and signal processing circuitry. The transmission circuitry causes an ultrasonic probe including a plurality of elements to transmit plane waves at a plurality of different deflection angles. The reception circuitry generates reception signal groups based on reflection waves that the individual elements included in the probe receive in response to the transmission of the plane waves. The signal processing circuitry acquires a plurality of complex images corresponding to the respective deflection angles and estimates wavefront distortion at the time of transmission using the complex pixel values of the complex images, and performs correction processing on the reception signal groups based on the wavefront distortion at the time of the transmission to generate image data based on the complex pixel values of the complex images for the respective deflection angles that are acquired from the reception signal groups after the correction processing.

19 Claims, 11 Drawing Sheets

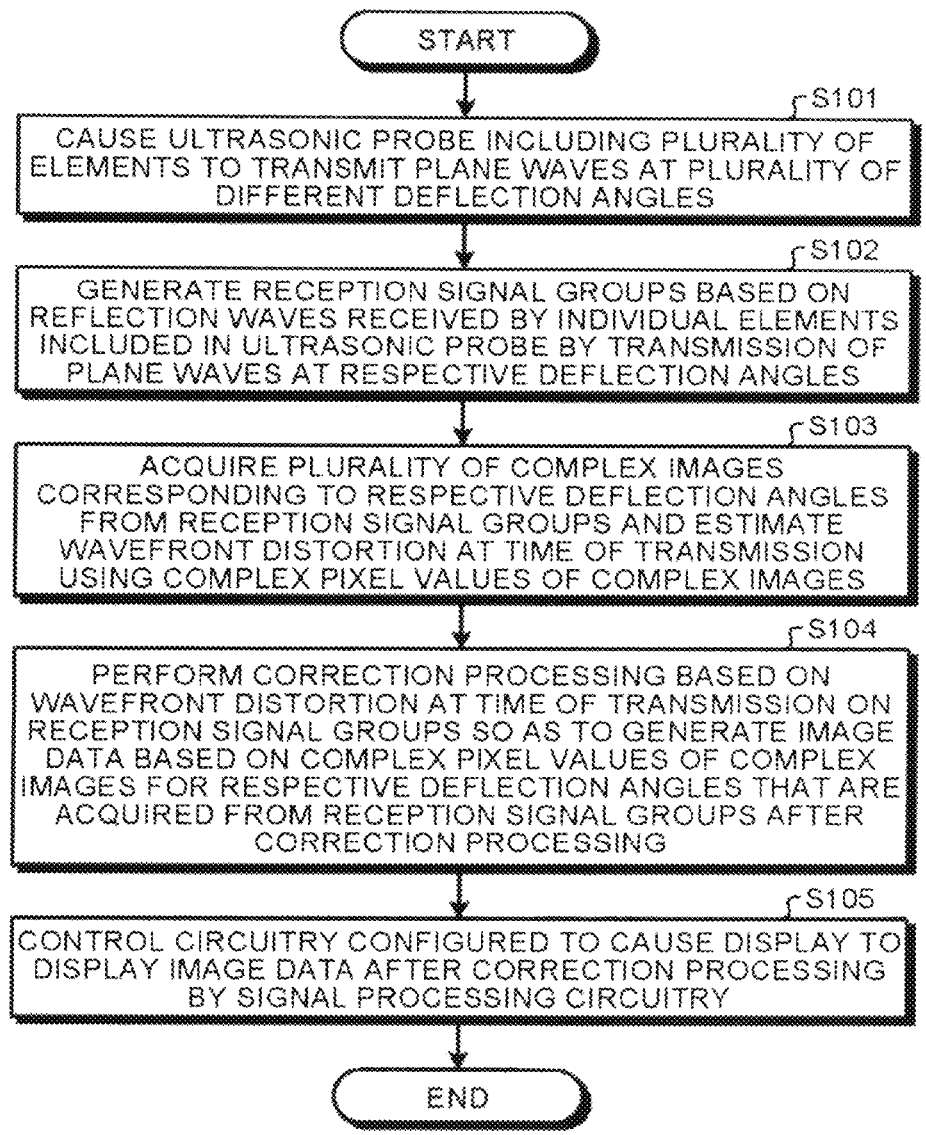

ULTRASONIC DIAGNOSTIC DEVICE AND CORRECTION METHOD

CROSS-REFERENCE TO RELATED APPLICATIONS

This application is based upon and claims the benefit of priority from Japanese Patent Application No. 2014-103715, filed on May 19, 2014, the entire contents of all of which are incorporated herein by reference.

FIELD

Embodiments described herein relate generally to an ultrasonic diagnostic device and a correction method.

BACKGROUND

Conventionally, when an ultrasonic image (for example, B mode image) is shot, transmission and reception beams are formed by setting transmission delay time and reception delay time using a sound velocity of a constant value under an assumption that the speed (sound velocity) of ultrasonic waves propagating in a living body in a scan range is constant. The sound velocity in the living body is, however, not necessarily constant and disturbance of the transmission and reception beams (disturbance of wavefronts) occurs and image quality deteriorates when the delay time is set based on the above-mentioned assumption.

For solving the above-mentioned problem, a method for estimating disturbance of wavefronts (wavefront distortion) using correlations among signals received by respective elements of an ultrasonic probe to correct the wavefront distortion has been developed. Furthermore, a method has been known for estimating and correcting wavefront distortion when plane waves at different deflection angles are transmitted and transmission wavefronts are synthesized based on reception signals received by respective elements to form a high-resolution image. In the above-mentioned methods, under an assumption that a layer (hereinafter, non-uniform layer) causing the sound velocity to be non-uniform in a propagation path of ultrasonic waves is in close contact with the ultrasonic probe, reception wavefront distortion is obtained from difference in delay time between reception channels and correction of the transmission wavefront distortion is repeatedly performed.

The non-uniform layer in the living body is not only in close contact with the ultrasonic probe but also it may present at a position distanced from the ultrasonic probe. In addition, the propagation path at the time of transmission is different from that at the time of reception. In the above-mentioned methods, an estimation result of the reception wavefront distortion is fed-back for correction of the transmission wavefront distortion on the different propagation path under the assumption that the non-uniform layer is in close contact with the ultrasonic probe. This means that the above-mentioned methods do not necessarily correct the wavefront distortion sufficiently.

BRIEF DESCRIPTION OF THE DRAWINGS

FIG. 11 is a flowchart of a processing procedure of the ultrasonic diagnostic device according to other embodiments.

DETAILED DESCRIPTION

An ultrasonic diagnostic device according to an embodiment includes transmission circuitry, reception circuitry, signal processing circuitry, and control circuitry. The transmission circuitry causes an ultrasonic probe including a plurality of elements to transmit plane waves at a plurality of different deflection angles. The reception circuitry generates reception signal groups based on reflection waves that the individual elements included in the ultrasonic probe receive in response to the transmission of the plane waves at the different deflection angles. The signal processing circuitry acquires a plurality of complex images corresponding to the respective deflection angles from the reception signal groups and estimates wavefront distortion at the time of transmission using the complex pixel values of the complex images. The signal processing circuitry performs correction processing on the reception signal groups based on the wavefront distortion at the time of the transmission to generate image data based on the complex pixel values of the complex images for the respective deflection angles that are acquired from the reception signal groups after the correction processing. The control circuitry causes a display to display the image data after the correction processing by the signal processing circuitry.

Hereinafter, embodiments of an ultrasonic diagnostic device and a correction method will be described in detail with reference to the accompanying drawings.

Embodiment

Figure 1:
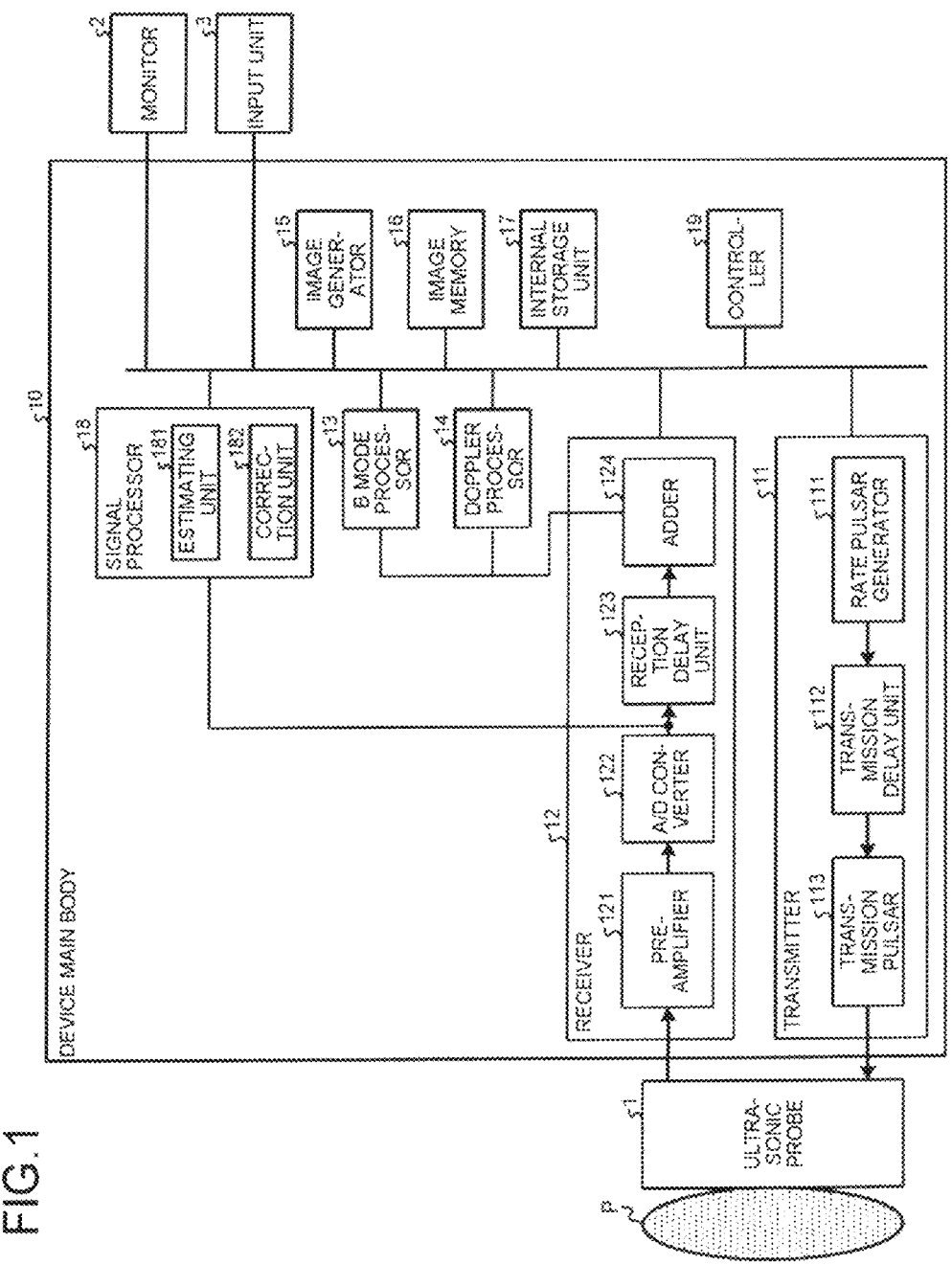
FIG. 1 is a block diagram illustrating an example of the configuration of an ultrasonic diagnostic device according to an embodiment.

First, the configuration of an ultrasonic diagnostic device according to the present embodiment is described. FIG. 1 is a block diagram illustrating an example of the configuration of the ultrasonic diagnostic device in the present embodiment. As illustrated in FIG. 1, the ultrasonic diagnostic device in an embodiment includes an ultrasonic probe 1, a monitor 2, an input unit 3, and a device main body 10.

The ultrasonic probe 1 includes a plurality of elements such as piezoelectric transducer elements and these elements generate ultrasonic waves based on a drive signal that is supplied from a transmitter 11 included in the device main body 10, which will be described later. The ultrasonic probe 1 receives reflection waves from a subject P and converts the reflection waves to electric signals. For example, the ultrasonic probe 1 includes matching layers that are provided on the piezoelectric transducer elements and backing members that prevent ultrasonic waves from propagating to the rear side from the piezoelectric transducer elements. It should be noted that the ultrasonic probe 1 is connected to the device main body 10 in a detachable manner.

When the ultrasonic probe 1 transmits ultrasonic waves to the subject P, the transmitted ultrasonic waves are reflected in succession by a surface having acoustic impedance discontinuity in tissues in the body of the subject P and are received by the elements included in the ultrasonic probe 1 as reflection waves. The reflection waves are converted into reflection wave signals, which are electric signals, at the elements that have received the reflection waves. The amplitude of the reflection wave signals generated on the respective transducer elements depends on difference in the acoustic impedance on the surface having acoustic impedance discontinuity by which the ultrasonic waves are reflected. The reflection wave signals when transmitted ultrasonic pulses are reflected by surfaces of blood flow, cardiac walls, and the like are subjected to frequency deviation by the Doppler effect depending on the velocity component of a moving body against the transmission direction of the ultrasonic waves.

In the present embodiment, the ultrasonic probe 1 that is connected to the device main body 10 is a probe capable of transmitting plane waves and capable of transmitting the plane waves in a plurality of directions (at a plurality of different deflection angles). For example, in the present embodiment, the ultrasonic probe 1 that is connected to the device main body 10 is a probe in which a plurality of fine elements having small radiation faces of ultrasonic waves are aligned so as to be capable of transmitting plane waves.

The input unit 3 includes a mouse, a keyboard, a button, a panel switch, a touch command screen, a foot switch, a track ball, a joystick, or the like, receives various setting requests from an operator of the ultrasonic diagnostic device, and transfers the received various setting requests to the device main body 10.

The monitor 2 displays a graphic user interface (GUI) for the operator of the ultrasonic diagnostic device to input various setting requests using the input unit 3, and displays ultrasonic image data and the like generated in the device main body 10, for example.

The device main body 10 is a device that generates ultrasonic image data based on the reflection wave signals generated by the respective transducer elements included in the ultrasonic probe 1. As illustrated in FIG. 1, the device main body 10 includes the transmitter 11, a receiver 12, a B mode processor 13, a Doppler processor 14, an image generator 15, an image memory 16, an internal storage unit 17, a signal processor 18, and a controller 19.

The transmitter 11 causes the ultrasonic probe 1 to transmit ultrasonic waves. As illustrated in FIG. 1, the transmitter 11 includes a rate pulsar generator 111, a transmission delay unit 112, and a transmission pulsar 113, and supplies a drive signal to the ultrasonic probe 1. The rate pulsar generator 111 repeatedly generates a rate pulse for forming transmission ultrasonic waves at a certain rate frequency (Pulse Repetition Frequency (PRF)). The rate pulse applies a voltage to the transmission pulsar 113 with transmission delay time that varies by passing through the transmission delay unit 112. For example, the transmission delay unit 112 gives transmission delay time for each piezoelectric transducer element that is necessary for focusing the ultrasonic waves generated from the ultrasonic probe 1 in a beam form and determining transmission directivity to each rate pulse generated by the rate pulsar generator 111. Alternatively, for example, the transmission delay unit 112 gives transmission delay time for each piezoelectric transducer element that is necessary for determining transmission directivity for transmission of the ultrasonic waves generated from the ultrasonic probe 1 as the plane waves to each pulse rate generated by the rate pulsar generator 111. The transmission pulsar 113 applies a drive signal (drive pulse) to the ultrasonic probe 1 at a timing based on the rate pulse. The transmitter 11 controls the number and positions (transmission openings) of transducer elements that are used for transmission of the ultrasonic waves and the transmission delay time in accordance with the position of each of the transducer elements constituting the transmission openings so as to give the transmission directivity.

The drive pulse is converted into mechanical vibration from an electric signal on the piezoelectric transducer elements after transmitted to the piezoelectric transducer elements in the ultrasonic probe 1 through a cable from the transmission pulsar 113. The mechanical vibration is transmitted as ultrasonic waves in the living body. The ultrasonic waves with the transmission delay time that varies for each piezoelectric transducer element are propagated in a predetermined direction while being focused or as plane waves. The transmission delay unit 112 changes the transmission delay time to be given to each rate pulse so as to adjust the transmission direction from the piezoelectric transducer element surface to be any direction. The transmission delay time is normally calculated from a sound velocity value set in advance as an average sound velocity of the tissues in the body of the subject P to be shot. The transmitter 11 creates a wavefront function based on a direction from the controller 19, which will be described later, so as to perform the above-mentioned transmission control.

The transmitter 11 has a function of instantaneously changing a transmission frequency, a transmission drive voltage, and the like in order to execute a certain scan sequence based on a direction from the controller 19, which will be described later. In particular, the transmission drive voltage can be changed by a linear amplifier-type oscillation circuit capable of instantaneously switching a value thereof or a mechanism of electrically switching a plurality of power supply units.

The reflection waves of the ultrasonic waves transmitted from the ultrasonic probe 1 reach the piezoelectric transducer elements in the ultrasonic probe 1, and then, are converted into electric signals (reflection wave signals) from mechanical vibration on the piezoelectric transducer elements and are input to the receiver 12. As illustrated in FIG. 1, the receiver 12 includes a pre-amplifier 121, an analog-to-digital (A/D) converter 122, a reception delay unit 123, and an adder 124, and performs various pieces of processing on the reflection wave signals received by the ultrasonic probe 1 so as to generate reflection wave data.

The pre-amplifier 121 amplifies the reflection wave signal for each channel so as to perform gain adjustment. The A/D converter 122 A/D-converts the reflection wave signal on which the gain correction has been performed so as to convert it to a digital signal. The reception delay unit 123 multiplies the digital signal by reception delay (reception delay time) necessary for determining reception directivity. To be specific, the reception delay unit 123 gives the reception delay time to the digital signal based on distribution of the reception delay time for each reception focus calculated from the sound velocity value set in advance as the average sound velocity of the tissues in the body of the subject P to be shot.

The adder 124 adds the digital signal multiplied by the reception delay time calculated based on the sound velocity so as to generate a reception signal subjected to phasing addition (reflection wave data). The addition processing by the adder 124 emphasizes reflection components from the direction in accordance with the reception directivity of the reflection wave signal. That is to say, the reception delay unit 123 and the adder 124 as illustrated in FIG. 1 are phasing-adders that execute a delay and sum (DAS) method with the reception delay based on the average sound velocity.

The signal that is output from the A/D converter 122 is an IQ signal (complex signal) formed by converting the reflection wave signal on which the gain correction has been performed into an in-phase (I) signal and a quadrature-phase (Q) signal in a base band by quadrature detection processing or Hilbert transformation processing, for example; and the same processing can be also performed on an RF signal in the present embodiment.

The device main body 10 in the present embodiment has a configuration in which the signal output from the A/D converter 122 can be also input to the signal processor 18 as illustrated in FIG. 1. The signal processor 18 is a processor that performs estimation processing of wavefront distortion and correction processing based on the wavefront distortion, instead of general DAS processing, using reception signal groups output from the A/D converter 122, and includes an estimating unit 181 and a correction unit 182 as illustrated in FIG. 1. Although not illustrated in the drawing, the signal processor 18 includes a signal storage unit such as a memory that stores therein the reception signal groups output from the A/D converter 122. Processing that is performed by the signal processor 18 will be described in detail later.

The B mode processor 13 performs logarithmic amplification, envelope detection processing, logarithmic compression, and the like on the reflection wave data output from the adder 124 so as to generate data (B mode data) in which signal intensity (amplitude intensity) at each sample point is expressed by brightness.

The Doppler processor 14 analyzes the frequency of the reflection wave data output from the adder 124 so as to generate data (Doppler data) formed by extracting motion information of the moving body (blood flow, tissues, contrast echo components, or the like) based on the Doppler effect. To be specific, the Doppler processor 14 generates Doppler data formed by extracting average sound velocity values, dispersion values, power values, and the like over a large number of points as the motion information of the moving body.

The image generator 15 generates ultrasonic image data from the pieces of data generated by the B mode processor 13 and the Doppler processor 14. In general, the image generator 15 converts (scan-converts) a scan line signal string for ultrasonic scan into a scan line signal string in a video format represented by a television or the like so as to generate ultrasonic image data for display. To be specific, the image generator 15 performs coordinate conversion in accordance with a scan mode of the ultrasonic waves by the ultrasonic probe 1 so as to generate the ultrasonic image data for display. The image generator 15 performs, as various pieces of image processing in addition to the scan conversion, image processing (smoothing processing) for regenerating an average value image of the brightness, image processing (edge emphasis processing) using a differential filter in the image, and the like using a plurality of image frames after the scan conversion, for example. The image generator 15 synthesizes pieces of character information, scales, body marks, and the like of various parameters on the ultrasonic image data.

The B mode data and the Doppler data are pieces of ultrasonic image data before the scan conversion processing and the data that is generated by the image generator 15 is ultrasonic image data for display after the scan conversion processing. The B mode data and the Doppler data are also referred to as raw data.

The image memory 16 is a memory storing therein the image data generated by the image generator 15. The image memory 16 can also store therein the pieces of data generated by the B mode processor 13 and the Doppler processor 14. The B mode data and the Doppler data that are stored in the image memory 16 can be called by the operator after diagnosis, for example, and become the ultrasonic image data for display through the image generator 15. The image memory 16 can also store therein the data output from the receiver 12 and the data output from the signal processor 18.

The internal storage unit 17 stores therein control programs for performing transmission and reception of the ultrasonic waves, the image processing, and the display processing, and various pieces of data such as diagnostic information (for example, patient ID and observations by doctors), diagnostic protocols, and various body marks. The internal storage unit 17 is also used for keeping data stored in the image memory 16, and so on, if necessary.

The controller 19 controls the processing of the ultrasonic diagnostic device as a whole. To be specific, the controller 19 controls the pieces of processing of the transmitter 11, the receiver 12, the B mode processor 13, the Doppler processor 14, the image generator 15, and the signal processor 16 based on various setting requests input from the operator through the input unit 3, and various control programs and various pieces of data read from the internal storage unit 17. The controller 19 controls the ultrasonic image data for display that is stored in the image memory 16 to be displayed on the monitor 2.

The entire configuration of the ultrasonic diagnostic device according to the present embodiment has been described above. The ultrasonic diagnostic device according to the present embodiment generates and displays ultrasonic image data (for example, B mode image data) with this configuration. In normal shooting of an ultrasonic image, under an assumption that the velocity (sound velocity) of ultrasonic waves propagating in the living body in a scan range is constant, the transmission delay time and the reception delay time are controlled using the sound velocity of a constant value set as the average sound velocity as described above, for example. The sound velocity in the living body is, however, not necessarily constant. For example, with the DAS processing using the average sound velocity, wavefront distortion at the time of transmission and wavefront distortion at the time of reception are generated and image quality of the B mode image data deteriorates.

Figure 2:
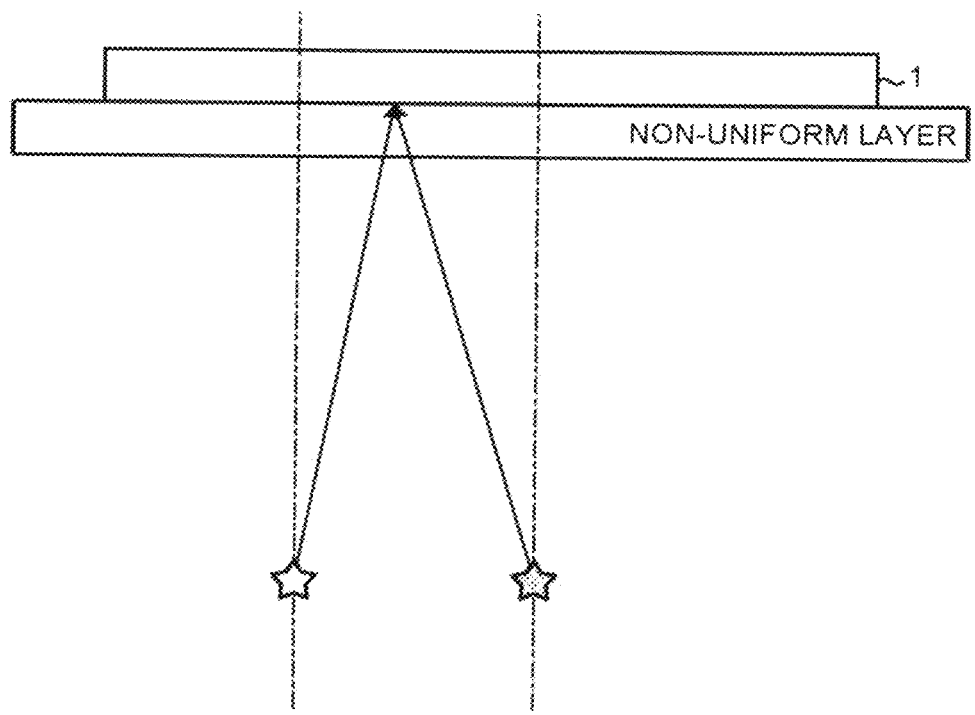
FIG. 2 is a first diagram for explaining a problem of a conventional technique.
Figure 3:
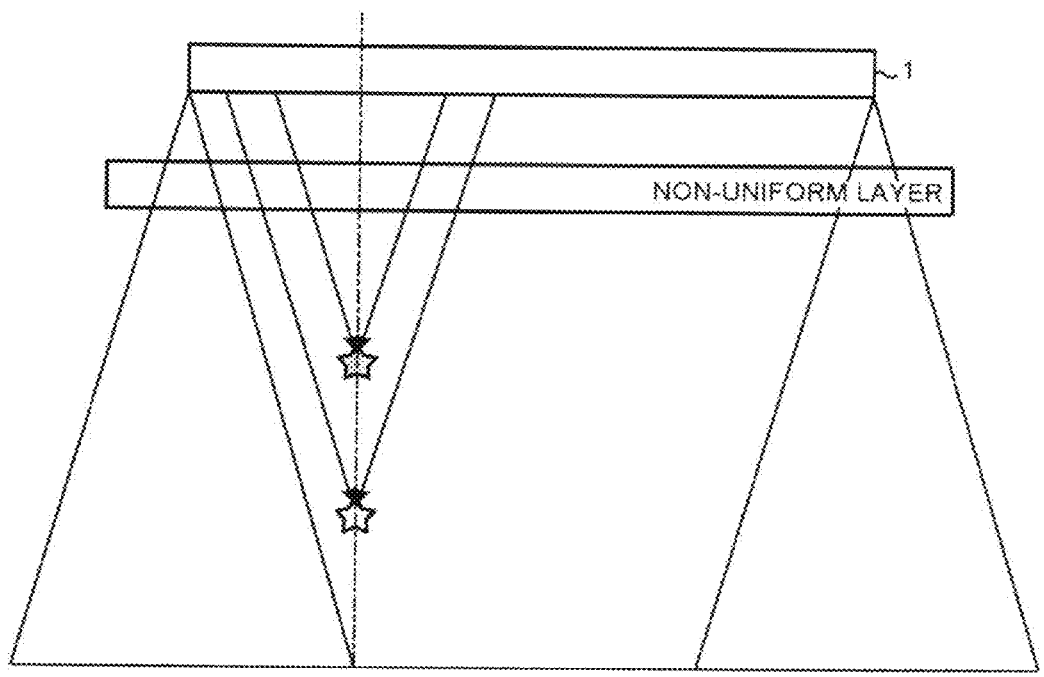
FIG. 3 is a second diagram for explaining the problem of the conventional technique.

For solving this problem, known has been a method in which when plane wave synthesis of transmitting a plurality of plane waves at a plurality of different deflection angles and synthesizing transmission wavefronts based on reception signals received by the respective elements so as to form a high-resolution image is performed, estimation and correction of the wavefront distortion are performed using correlations among the signals received by the respective elements of the ultrasonic probe 1. FIG. 2 and FIG. 3 are diagrams for explaining the problem of the conventional technique.

As illustrated in FIG. 2, in the above-mentioned conventional technique, under an assumption that a "non-uniform layer" causing the sound velocity to be non-uniform in a propagation path of ultrasonic waves is in close contact with an abutment surface of the ultrasonic probe 1, reception wavefront distortion is obtained from difference in delay time between reception channels and correction of distortion (transmission wavefront distortion) of plane wavefronts that are transmitted at respective deflection angles is repeatedly performed. That is to say, the above-mentioned conventional technique is a method that is effective under the assumption that disturbance of the wavefront similar to that at the time of reception can be considered to occur at the time of transmission in the same manner as long as the non-uniform layer is in close contact with the ultrasonic probe 1.

As illustrated in FIG. 3, however, the non-uniform layer in the living body is not only in close contact with the ultrasonic probe 1 but also it may present at a position distanced from the ultrasonic probe 1. Reception wavefronts incident on the same element are influenced by the non-uniform layer at substantially the same position, so that the reception wavefront distortion can be estimated by the above-mentioned method. As illustrated in FIG. 3, however, when the deflection angle of the transmission wavefront is large, the propagation path of the transmission wavefront is different among sample points (pixels) having different depths even on the same reception scan line. The above-mentioned method is not effective under normal conditions because an estimation result of the reception wavefront distortion is fed back for correction of the transmission wavefront distortion on a different propagation path under the assumption that the non-uniform layer is in close contact with the ultrasonic probe 1.

In the present embodiment, processing by the signal processor 18 as illustrated in FIG. 1 is performed in order to correct the wavefront distortion with higher accuracy.

First, the transmitter 11 in the present embodiment causes the ultrasonic probe 1 including a plurality of elements (plurality of fine elements) to transmit plane waves at a plurality of different deflection angles. The receiver 12 generates reception signal groups based on reflection waves received by the individual elements included in the ultrasonic probe 1 by transmission of the plane waves at the respective deflection angles. To be specific, the above-mentioned reception signal groups are complex signal groups formed by converting signals based on the reflection waves received by the individual elements included in the ultrasonic probe 1 by quadrature detection or Hilbert transformation. To be more specific, the above-mentioned reception signal groups are IQ signals before being multiplied by reception delay output from the A/D converter 122.

The estimating unit 181 acquires the complex image groups corresponding to the respective deflection angles from the reception signal groups and estimates wavefront distortion at the time of transmission (transmission wavefront distortion) using complex pixel values of the complex image groups at the same positions. The correction unit 182 performs correction processing based on the wavefront distortion at the time of transmission on the reception signal groups so as to generate image data based on the complex pixel values of the complex images corresponding to the respective deflection angles at the same positions that are acquired from the reception signal groups after the correction processing.

In other words, the estimating unit 181 acquires a plurality of complex images corresponding to a plurality of deflection angles from the reception signal groups and estimates the wavefront distortion at the time of transmission using complex pixel values of the plurality of acquired complex images. The correction unit 182 performs correction processing based on the wavefront distortion at the time of transmission on the reception signal groups so as to generate image data based on the complex pixel values of the complex images for the respective deflection angles that are acquired from the reception signal groups after the correction processing.

In the present embodiment, the estimating unit 181 further estimates wavefront distortion (reception wavefront distortion) at the time of reception using the reception signal groups and the correction unit 182 performs correction processing using the wavefront distortion at the time of reception on the reception signal groups. In the present embodiment, the controller 19 controls the estimating unit 181 and the correction unit 182 to repeat the estimation processing of the wavefront distortion at the time of transmission and the correction processing based on the wavefront distortion at the time of transmission and the estimation processing of wavefront distortion at the time of reception and the correction processing based on the wavefront distortion at the time of reception a plurality of times.

To be specific, the estimating unit 181 performs the pieces of estimation processing of the wavefront distortion at the time of transmission and reception by calculating an eigenvector corresponding to a maximum eigenvalue of a covariance matrix. To be more specific, the estimating unit 181 multiplies the complex signal groups (IQ signal groups as the reception signal groups) by delay for focusing on each pixel on an image so as to calculate a complex signal sequence for reconstructing each pixel. The estimating unit 181 calculates the covariance matrix using each complex signal sequence and calculates an eigenvector corresponding to a maximum eigenvalue of the covariance matrix for each pixel or a matrix formed by cumulating or averaging covariance matrices for a plurality of pixels. The above-mentioned classification is performed in accordance with the size of an image region, which will be described later.

The method for estimating the wavefront distortion at the time of transmission and reception that is performed using the covariance matrix by the estimating unit 181 is a method in which elements in the reception wavefront distortion estimation and the transmission deflection angles in the transmission wavefront distortion estimation are handled in the same manner and transmission wavefront distortion for each deflection angle is estimated and reception wavefront distortion for each element is estimated such that image energy is the largest in a pixel group of a certain limited region while focusing on the fact that "pixel values are the same at the same positions among images formed by transmission of the plane waves at different deflection angles". With the estimation method, limitation on the non-uniform layer is largely reduced in comparison with the above-mentioned conventional technique. For example, the estimating unit 181 can estimate, as the wavefront distortion at the time of transmission, the wavefront distortion generated by a non-uniform medium (non-uniform layer) in the living body and the wavefront distortion generated by difference between the average sound velocity in the living body and the sound velocity (for example, average sound velocity) initially set with high accuracy.

In the above-mentioned estimation processing, in order to further reduce limitation on the position of the non-uniform layer, a region (video image formation region) on which a video image is formed by transmission of the plane waves is divided into a plurality of image regions. The estimating unit 181 performs the wavefront distortion estimation processing on each of the image regions and the correction unit 182 performs the correction processing based on the wavefront distortion estimated by the estimating unit 181 on each of the image regions.

Figure 4:
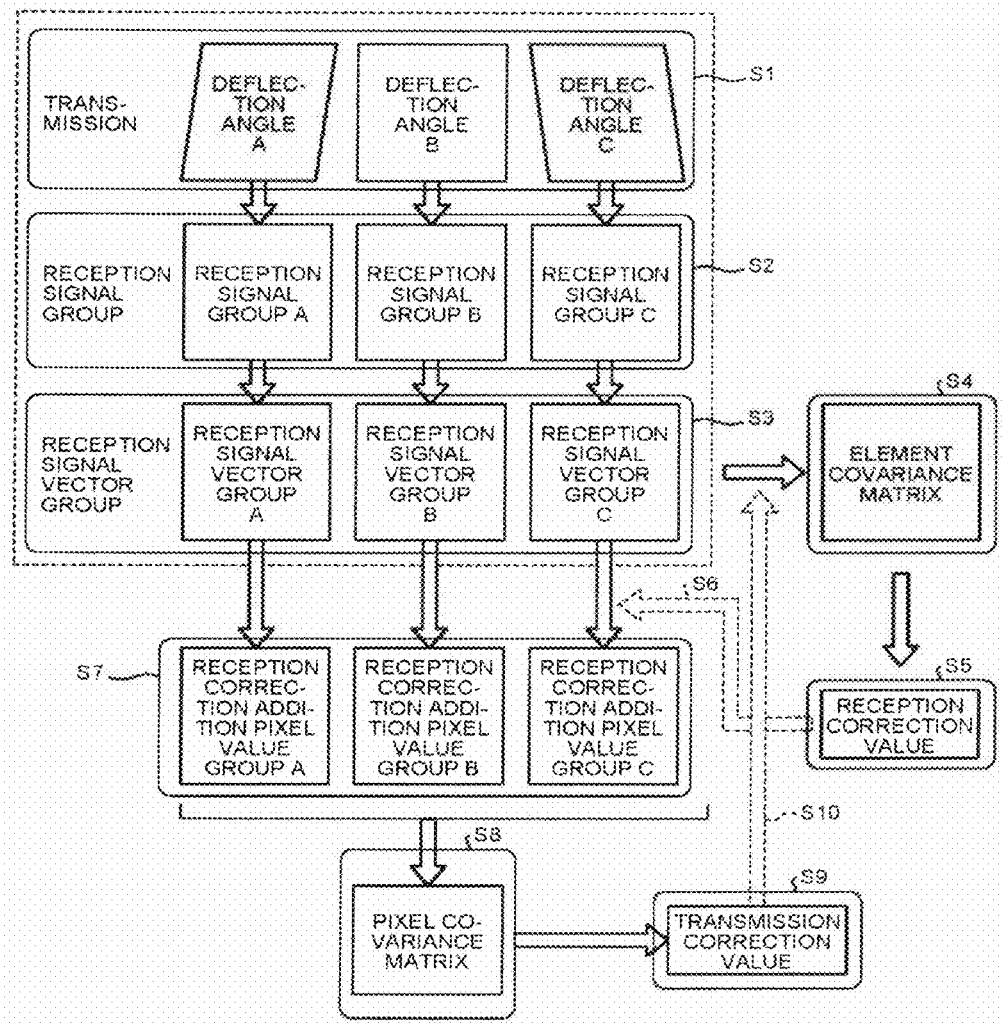
FIG. 4 is a first diagram for explaining an example of processing by a signal processor in the embodiment.
Figure 5:
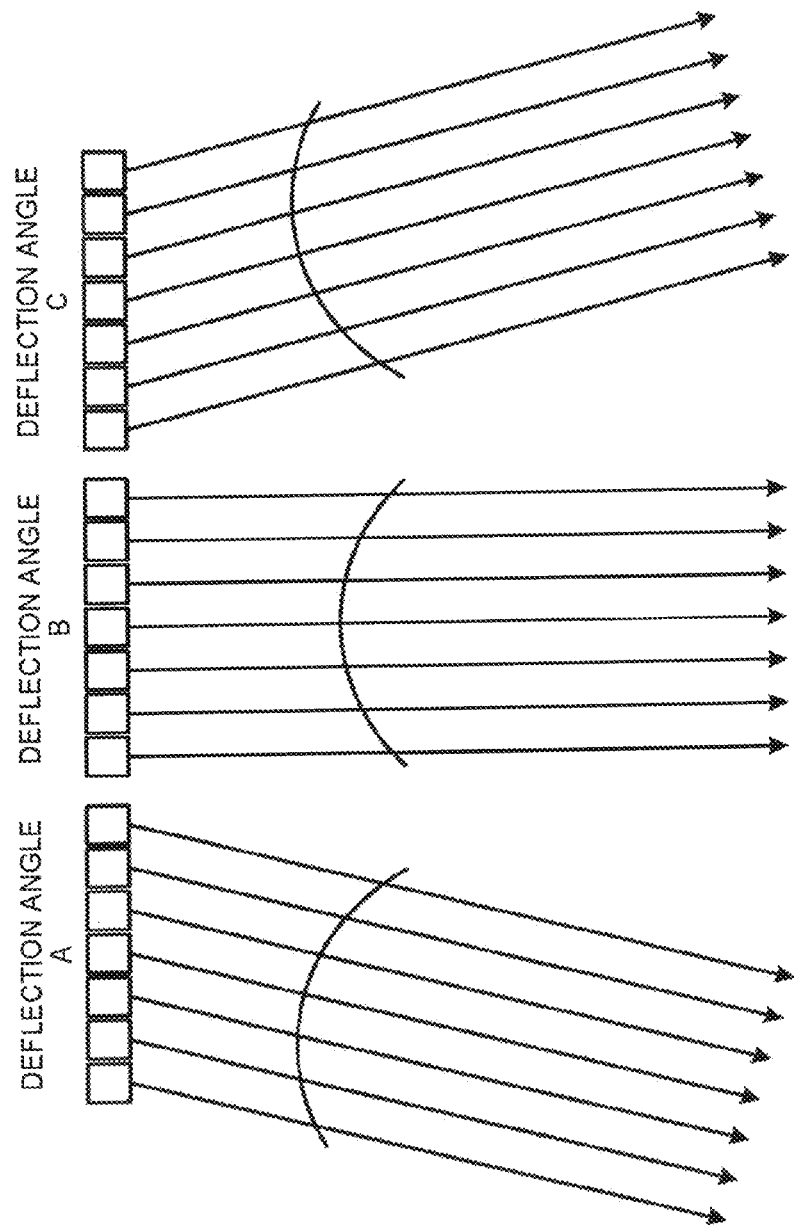
FIG. 5 is a second diagram for explaining the example of processing by the signal processor in the embodiment.
Figure 6:
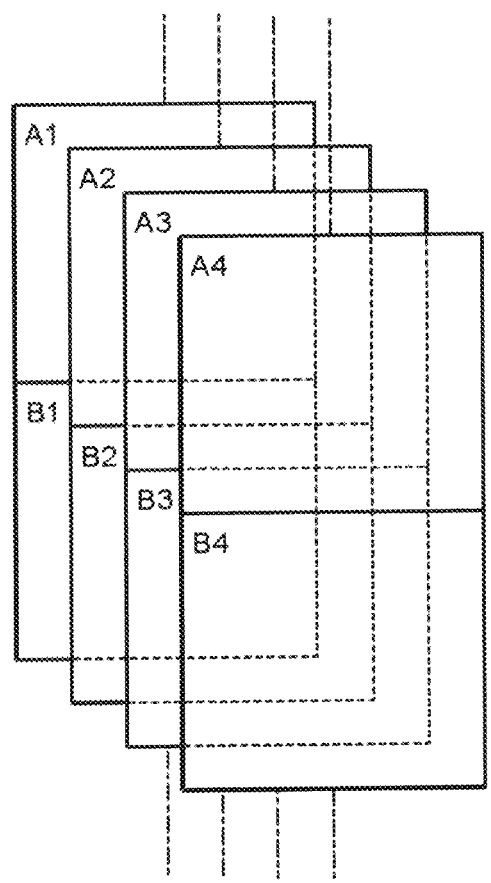
FIG. 6 is a third diagram for explaining the example of processing by the signal processor in the embodiment.

The following describes a specific example of the above-mentioned processing in detail with reference to FIG. 4 to FIG. 6 and the like. FIG. 4 to FIG. 6 are diagrams for explaining an example of processing by the signal processor in the present embodiment.

First, as indicated at step S1 in FIG. 4, the transmitter 11 transmits plane waves at a deflection angle A in the leftward direction, plane waves at a deflection angle B in the frontward direction, and plane waves at a deflection angle C in the rightward direction. As indicated at step S2 in FIG. 4, the A/D converter 122 of the receiver 12 generates a reception signal group A for the deflection angle A, a reception signal group B for the deflection angle B, and a reception signal group C for the deflection angle C. The A/D converter 122 of the receiver 12 outputs them to the signal storage unit of the signal processor 18 based on a direction from the controller 19. Each of the reception signal groups A to C is an IQ signal group.

When the reception signal groups A to C are stored in the signal storage unit, for example, the estimating unit 181 performs estimation of reception wavefront distortion as first processing. First, the estimating unit 181 multiplies the reception signal group A by time delay so as to focus on each pixel on a reception delay pattern (see, left view in FIG. 5) at the deflection angle A calculated from an initial value (for example, average sound velocity). The estimating unit 181 multiplies the reception signal group B by delay so as to focus on each pixel on a reception delay pattern (see, center view in FIG. 5) at the deflection angle B calculated from the average sound velocity. The estimating unit 181 multiplies the reception signal group C by delay so as to focus on each pixel on a reception delay pattern (see, right view in FIG. 5) at the deflection angle C calculated from the average sound velocity.

With this processing, the estimating unit 181 calculates a reception signal vector group A, a reception signal vector group B, and a reception signal vector group C in a state of being multiplied by the delay time for reconstructing each pixel as indicated in step S3 in FIG. 4. The reception signal vector groups A to C that are calculated at step S3 of the first processing in the first round are provided by multiplication by the delay time under an assumption that there is no wavefront distortion. For example, the estimating unit 181 generates a reception signal vector "$R_j$" while using a complex signal sequence for reconstructing a "j"th pixel as a column vector based on the following equation (1):

$$R_j = [r_{j,1} \ldots r_{j,M}] \quad (1)$$

where "M" in the equation (1) is the total number of elements used for providing "$R_j$", and is the number of receiving elements used for reconstructing the "j"th pixel, for example. In the above equation, "$1 \leq m \leq M$, m is an integer" is satisfied. With use of the definition, "$r_{j,m}$" configuring the reception signal vector "$R_j$" is a complex signal provided by adding (or adding and averaging) the IQ signal at the deflection angle A, the IQ signal at the deflection angle B, and the IQ signal at the deflection angle C received by an "m"th element that have been multiplied by delay for reconstructing the "j"th pixel.

In the above equation, the time delay is multiplied for focusing, so that a complex pixel value "$I_j$" of the "j"th pixel can be calculated by the following equation (2):

$$I_j = R_j V^T \quad (2)$$

where "$V^T$" in the equation (2) is a transposed matrix of a column vector "V" for normalizing the IQ signal for each element, and for example, "V" is a column vector as indicated in the following equation (3):

$$V = [1/\sqrt{M} \ldots 1/\sqrt{M}] \quad (3)$$

As a pixel value on the complex image, for example, the square of an absolute value of the complex pixel value is used. In such a case, the pixel value of the "j"th pixel of the complex image is calculated by the following equation (4):

$$|I_j|^2 = I_j {}^*I_j = (R_j V^T)^*(R_j V^T) = V R_j {}^*R_j V^T = V(R_j {}^*R_j)V^T \quad (4)$$

where "$R_j \times R_j$" in the parentheses in the right side of the equation (4) is a covariance matrix of the reception signal vector "$R_j$". For example, as illustrated in FIG. 6, the video formation region is divided into an "image region A1, an image region A2, an image region A3, an image region A4 . . . , an image region B1, an image region B2, an image region B3, an image region B4 . . . " in both of the azimuth direction and the depth direction. The plurality of image regions as illustrated in FIG. 6 are set in a divided manner such that they overlap on each other partially in both of the azimuth direction and the depth direction.

If the "j"th pixel is a pixel in the image region B2, cumulating pixel values of all the pixels configuring the image region B2 leads to the following equation (5):

$$\Sigma |I_j|^2 = \Sigma V(R_j {}^*R_j)V^T = V\{\Sigma(R_j {}^*R_j)\}V^T \quad (5)$$

The sum of the covariance matrices in the brackets in the right side of the equation (5) is a matrix that the estimating unit 181 uses for estimation of the reception wavefront distortion. Where "Ve" is an eigenvector corresponding to a maximum eigenvalue "$\lambda_{max}$" of the "matrix of the sum of the covariance matrices" in the right side of the equation (5), the following equation (6) is established:

$$Ve\{\Sigma(R_j {}^*R_j)\}Ve^T = \lambda_{max} \quad (6)$$

The eigenvector "Ve" corresponding to "$\lambda_{max}$" is a vector "V" with which the total of the pixel values in the image region is maximum. That is to say, the eigenvector "Ve" is, for example, a vector that focuses on the respective pixels on the image region B2 most preferably. In other words, "Ve" is a value indicating distortion (phase difference) between the reception wavefronts received by the respective elements and ideal reception wavefronts on the respective values.

As indicated at step S4 in FIG. 4, the estimating unit 181 calculates an "element covariance matrix" that is the "matrix of the sum of the covariance matrices" on each of the image regions. The "element covariance matrix" as illustrated in FIG. 4 is a matrix of "M rows×M columns". It should be noted that the estimating unit 181 may calculate an average matrix of the covariance matrices of all the pixels in the image region as an "element covariance matrix". When the number of pixels contained in each image region is "1", the estimating unit 181 calculates "$R_j \times R_j$" as the "element covariance matrix". In the present embodiment, the entire video image formation region (scan range) may be set to one image region.

As indicated at step S5 in FIG. 4, the estimating unit 181 calculates an eigenvector "Ve" for each of the image regions from the element covariance matrix of each of the image regions and outputs the eigenvector "Ve" as a "reception correction value" to the correction unit 182. The eigenvector "Ve" is a vector in which reception correction values for the respective elements are aligned.

Then, the correction unit 182 performs second processing. To be specific, the correction unit 182 multiplies the reception signal vector group A, the reception signal vector group B, and the reception signal vector group C by the eigenvector "Ve" as the "reception correction value" for each of the image regions (step S6 in FIG. 4). With this processing, as indicated at step S7 in FIG. 4, the correction unit 182 calculates a reception correction addition pixel value group A, a reception correction addition pixel value group B, and a reception correction addition pixel value group C. That is to say, the correction unit 182 calculates a reception-corrected reception signal vector group A so as to calculate the reception correction addition pixel value group A as illustrated in FIG. 4. In the same manner, the correction unit 182 calculates a reception-corrected reception signal vector group B so as to calculate the reception correction addition pixel value group B as illustrated in FIG. 4. Furthermore, the correction unit 182 calculates a reception-corrected reception signal vector group C so as to calculate the reception correction addition pixel value group C as illustrated in FIG. 4. Each of the pixel values configuring the reception correction addition pixel value group is a complex pixel value.

The estimating unit 181 estimates the transmission wavefront distortion as third processing. First, the estimating unit 181 generates pixel vectors aligned for the respective deflection angles for the pixels at the same positions from the reception correction addition pixel value groups for the respective deflection angles that have been provided by the second processing. For example, the estimating unit 181 aligns a complex pixel value of the "j"th pixel for the deflection angle A, a complex pixel value of the "j"th pixel for the deflection angle B, a complex pixel value of the "j"th pixel for the deflection angle C so as to generate a pixel vector of the "j"th pixel at the same position. The pixel vector contains information related to wavefront distortion at a time point at which the transmission wavefronts at the respective deflection angles reach the same position.

It should be noted that the number of elements of the pixel vector is "N" where "N" is the number of a plurality of different deflection angles. For example, a pixel vector "$P_j$" of the "j"th pixel is "$P_j=[P_{j,1}, \ldots, P_{j,N}]$".

Then, the estimating unit 181 calculates a covariance matrix "$P_j \times P_j$" of the pixel vector "$P_j$". The estimating unit 181 derives a "pixel covariance matrix" as a "matrix of the sum of the covariance matrices" for each of the image regions as illustrated in FIG. 6, for example (step S8 in FIG. 4). The "pixel covariance matrix" as illustrated in FIG. 4 is a matrix of "N rows×N columns". As indicated at step S9 in FIG. 4, the estimating unit 181 calculates an eigenvector "Vt" corresponding to a maximum eigenvalue of the pixel covariance matrix for each of the image regions as a "transmission correction value". Then, the estimating unit 181 outputs the calculated "transmission correction value" to the correction unit 182.

Like "Ve", the above-mentioned eigenvector "Vt" is also a vector with which the total pixel value in the image region is a maximum and is a vector focusing on the respective pixels on the image region most preferably. "Vt" is a value indicating distortion (phase difference) between a transmission wavefront at each reflection angle that has reached the same position and an ideal transmission wavefront at each reflection angle that is to reach the same position. The eigenvector "Vt" is a vector in which transmission correction values for the respective deflection angles are aligned.

Subsequently, the correction unit 182 performs fourth processing. To be specific, the correction unit 182 multiplies the reception signal vector group A, the reception signal vector group B, and the reception signal vector group C by the eigenvector "Vt" as the "transmission correction value" for each of the image regions (step S10 in FIG. 4). With this, the correction unit 182 calculates a transmission-corrected reception signal vector group A, a transmission-corrected reception signal vector group B, and a transmission-corrected reception signal vector group C.

Thereafter, the first processing to the fourth processing using the transmission-corrected reception signal vector groups A to C in a first round are performed based on a direction from the controller 19. The first processing to fourth processing are repeated three times, for example, in accordance with setting information by the operator or a direction from the controller 19 based on initial setting. In this case, the correction unit 182 calculates complex signal values of the respective pixels from the transmission-corrected reception signal vector group A provided in the correction processing in the third round, calculates complex signal values of the respective pixels from the transmission-corrected reception signal vector group B provided in the correction processing in the third round, and calculates complex signal values of the respective pixels from the transmission-corrected reception signal vector group C provided in the correction processing in the third round. Then, the correction unit 182 outputs image data having, as pixel values, absolute values of complex signal values obtained by adding (or adding and averaging) three complex signal values of the respective pixels to the controller 19 as image data on which the correction processing has been performed. Then, the monitor 2 displays the image data on which the correction processing has been performed in accordance with a direction from the controller 19. In other words, the controller 19 causes the monitor 2 to display the image data on which the correction unit 182 has performed the correction processing.

Figure 7:
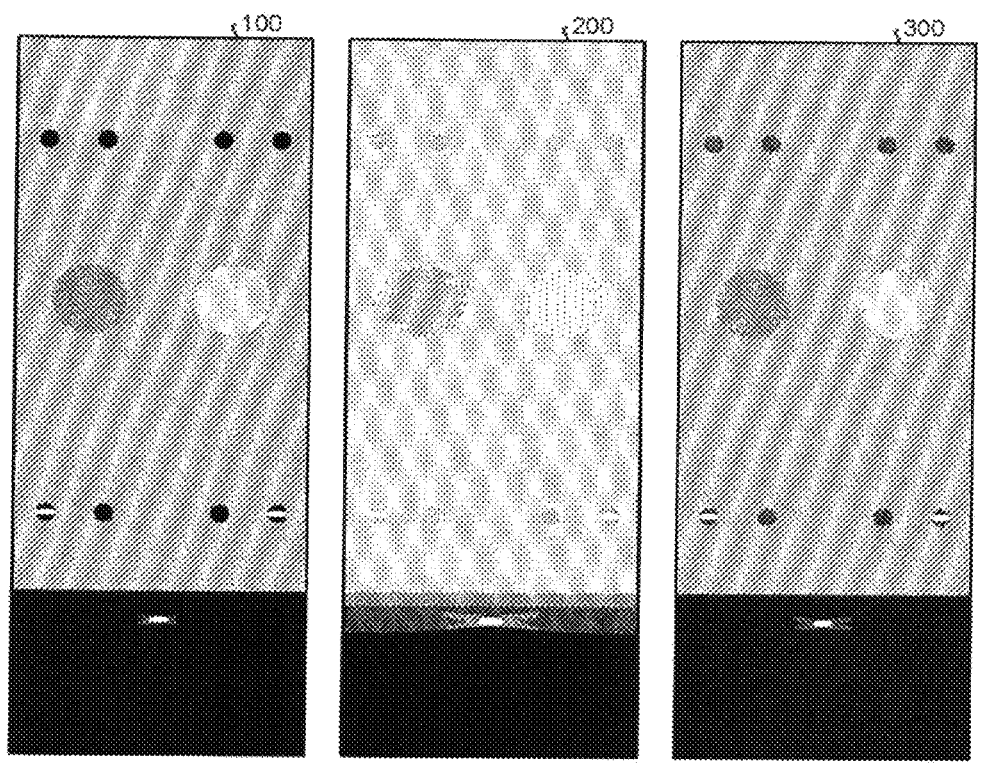
FIG. 7 is a diagram for explaining an effect of the embodiment.

FIG. 7 is a diagram for explaining an effect of the present embodiment. Image data 100 as illustrated in FIG. 7 is complex image data formed by synthesizing plane waves in an ideal state with a uniform medium where the sound velocity in the living body is constant. Image data 200 as illustrated in FIG. 7 is complex image data formed by synthesizing plane waves with deteriorating image quality due to wavefront distortion at the time of transmission and reception that has been generated by the non-uniform layer. Image data 300 as illustrated in FIG. 7 is image data (complex image data) that is output from the correction unit 182 by repeating the above-mentioned first processing to fourth processing three times. FIG. 7 indicates that the image data 300 has substantially the same image quality as the image data 100. That is to say, the image data 300 is image data formed after the transmission wavefront distortion and the reception wavefront distortion are corrected.

It should be noted that the controller 19 may display pieces of image data before and after the correction processing by the correction unit 182 on the monitor 2 simultaneously or in a switching manner. For example, the image data before the correction processing is the image data 200 formed by adding (or adding and averaging) complex images of the reception signal vector groups A to C generated using a set sound velocity as an initial value. For example, when the monitor 2 performs simultaneous display, the pieces of image data before and after the correction processing are displayed in parallel in accordance with a direction from the controller 19 that has received a direction from the operator. Alternatively, for example, the monitor 2 displays the pieces of image data before and after the correction processing in a switching manner in accordance with a direction from the controller 19 that has received a direction from the operator. The display control enables the operator to check the effect of the correction processing.

As described above, in the present embodiment, the elements in the estimation of reception wavefront distortion and the transmission deflection angles in the estimation of transmission wavefront distortion are handled in the same manner while focusing on the fact that "pixel values are the same at the same positions among images formed by transmission of the plane waves at different deflection angles". Furthermore, in the present embodiment, the transmission wavefront distortion for each deflection angle is estimated and the reception wavefront distortion for each element is estimated such that image energy is the largest in a certain limited pixel group. As the transmission wavefront distortion and the reception wavefront distortion that are estimated in the present embodiment, wavefront distortion generated by the non-uniform medium (non-uniform layer) in the living body and wavefront distortion generated by difference between the average sound velocity in the living body and the initially set sound velocity (for example, average sound velocity) can be also estimated with high accuracy.

It is reported that the distortion (time difference) due to the non-uniformity in the living body has equal to or lower than 1 wavelength in many cases. Accordingly, phase correction processing using the transmission wavefront distortion and the reception wavefront distortion that are estimated in the present embodiment can recover the accuracy of focusing sufficiently. Although the phase correction processing may possibly lower the resolution in an axial direction (reception scan line direction), it is expected that the lowering of the resolution is equal to or lower than 1 wavelength. Accordingly, in the present embodiment, the wavefront distortion can be corrected with higher accuracy. As a result, the present embodiment can provide an image with high image quality.

The calculation of the reception correction value and the transmission correction value that is employed in the present embodiment requires a relatively less operation amount without product-sum operation in the time direction unlike operation processing of a cross-correlation function. In the present embodiment, non-uniformity of distortion among the elements and non-uniformity of distortion among the deflection angles are estimated so as to make them most suitable to each of the image regions. Accordingly, in the present embodiment, it is possible to easily provide stable correction having high noise resistance.

In the present embodiment, the correction unit 182 may convert wavefront distortion (reception correction value and transmission correction value) estimated as the phase difference by the estimating unit 181 into distortion of propagation time and perform correction processing in the above-mentioned second processing and fourth processing. Also with this modification, the correction unit 182 can output image data on which both of the wavefront distortion at the time of transmission and the wavefront distortion at the time of reception have been corrected.

For example, upon receiving a request from the operator for referencing in a time series manner pieces of image data on which the correction processing has been performed, the transmitter 11 continuously transmits plane waves at a plurality of deflection angles. In such a case, the correction unit 182 sets the wavefront distortion (reception correction value and transmission correction value), used in the correction processing when image data in a certain frame is output, to another wavefront distortion (reception correction value and transmission correction value) to be used for correction processing for outputting image data from the next frame of the frame. This modification can reduce an operation amount for calculating a reception correction value and a transmission correction value each suitable for shooting a moving image.

In the above-mentioned embodiment, a plurality of image regions are regions formed by dividing an image formation region into a plurality of regions in each of the azimuth direction and the depth direction. In the above-mentioned embodiment, however, a modification can be made in which the plurality of image regions may be either regions formed by dividing the image formation region into a plurality of regions in the azimuth direction or regions formed by dividing the image formation region into a plurality of regions in the depth direction. Also in this case, limitation on the non-uniform layer can be reduced. In order to calculate the reception correction value and the transmission correction value stably with high accuracy, however, regardless of the position of the non-uniform layer, it is preferable that the plurality of image regions divided in each of the azimuth direction and the depth direction be used.

In the above-mentioned embodiment, the number of repetition times of the first processing to fourth processing is set in advance. The above-mentioned embodiment may be modified into a modification in which the correction unit 182 determines whether the correction processing is performed in accordance with the degree of wavefront distortion estimated by the estimating unit 181. For example, when the number of repetition times is set to six and a transmission correction value output from the estimating unit 181 in the third processing in the fourth round is substantially equivalent to or larger than a transmission correction value output from the estimating unit 181 in the third processing in the third round, the correction unit 182 does not perform the correction processing using the transmission correction value output from the estimating unit 181 in the third processing in the fourth round and performs the correction processing using the transmission correction value output from the estimating unit 181 in the third processing in the third round to output image data after the correction processing. In this modification, output of image data with image quality deteriorated, instead of improved, due to unnecessary correction processing can be avoided.

In the above-mentioned embodiment, modifications as illustrated in FIGS. 8A, 8B, and 8C and FIG. 9 may be provided. FIGS. 8A, 8B, and 8C and FIG. 9 are diagrams for explaining the modifications of the present embodiment.

In the above-mentioned embodiment, the same image regions are used in the calculation of the reception correction value and the transmission correction value. In the above-mentioned embodiment, however, the image regions may be formed by division with a pattern that is different between the estimation processing of the wavefront distortion at the time of transmission and the estimation processing of the wavefront distortion at the time of reception.

Figure 8A:
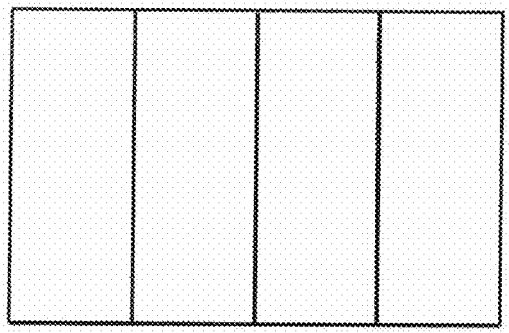
FIGS. 8A, 8B, and 8C are first diagrams for explaining modifications of the embodiment.

For example, as described above, it is supposed that the reception wavefront distortion at individual sample points on the same reception scan line is relatively less fluctuated. In view of this point, as illustrated in FIG. 8A, the controller 19 directs the estimating unit 181 to estimate the reception wavefront distortion using individual image regions formed by dividing the video image formation region in the azimuth direction, for example.

Figure 8B:
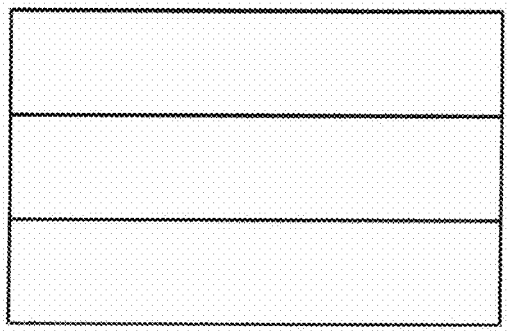

On the other hand, as described above, the transmission wavefront distortion largely fluctuates even at individual sample points on the same reception scan line due to the difference in the propagation path caused by the difference in the deflection angle. In view of this point, as illustrated in FIG. 8B, the controller 19 directs the estimating unit 181 to estimate the transmission wavefront distortion using individual image regions formed by dividing the video image formation region in the depth direction, for example. It should be noted that the individual image regions as illustrated in FIG. 8A and FIG. 8B may overlap on each other as in the individual image regions as illustrated in FIG. 6.

Figure 8C:
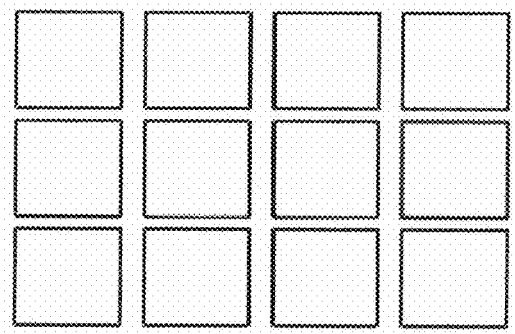

Alternatively, the plurality of image regions may be set by dividing the video image formation region discretely as illustrated in FIG. 8C, for example. In this case, the estimating unit 181 estimates wavefront distortion on regions other than the plurality of image regions by spatial interpolation processing using the wavefront distortion (transmission wavefront distortion and reception wavefront distortion) estimated on the respective image regions. With this modification, the estimating unit 181 can reduce operation amounts necessary for the estimation processing of the wavefront distortion at the time of transmission and the estimation processing of the wavefront distortion at the time of reception.

Figure 9:
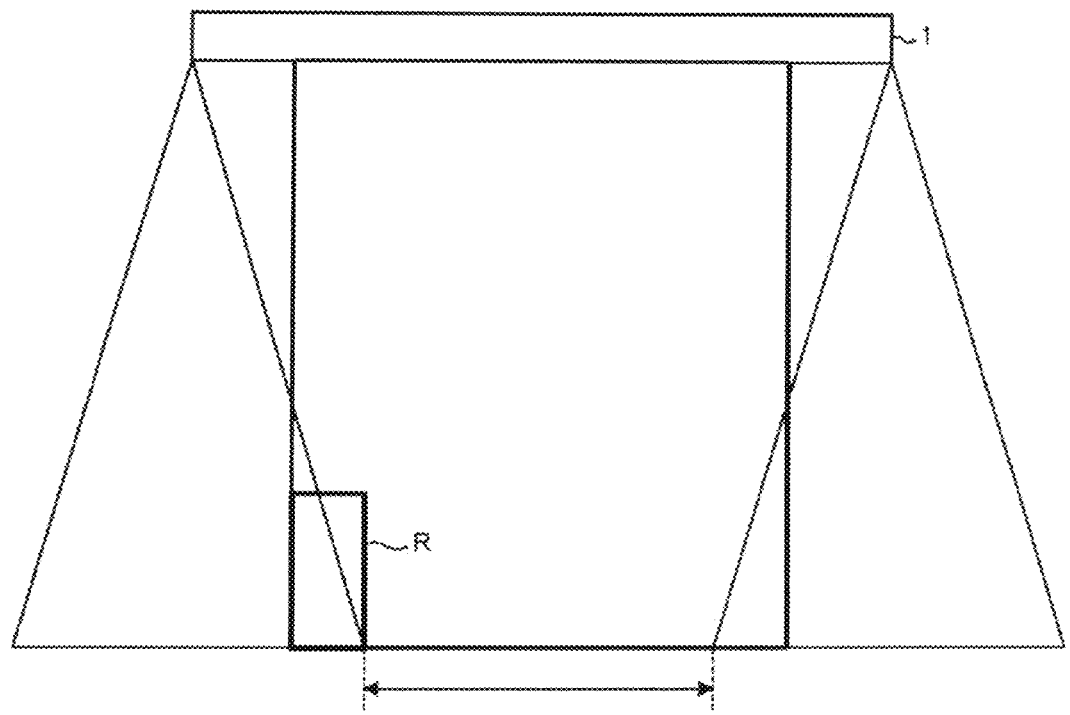
FIG. 9 is a second diagram for explaining another modification of the embodiment.

Furthermore, the estimating unit 181 and the correction unit 182 may perform the pieces of processing on a region specified as a region for providing image data after correction in a region that is scanned by transmission of the plane waves at a plurality of deflection angles. For example, when plane waves inclined to the right or left sides with large deflection angles are transmitted, there is a region R in which the transmission waves are not the plane waves on certain regions of the video image formation region as illustrated in FIG. 9. When synthesis of the plane waves is performed on the region R, vertical stripes called moire are generated frequently. To avoid this situation, the controller 19 or the operator directs the estimating unit 181 and the correction unit 182 to set only a region indicated by a double-headed arrow as indicated in FIG. 9 as a target of the first processing to the fourth processing, for example. In this modification, the region set as the target of the first processing to the fourth processing is limited so as to reduce operation amounts necessary for the estimation processing of the wavefront distortion at the time of transmission and the estimation processing of the wavefront distortion at the time of reception and enhance an image quality improvement effect by the synthesis of the plane waves more reliably.

In the above-mentioned embodiment, the correction unit 182 sets the eigenvector as the correction value that is used for the correction processing based on the wavefront distortion estimated by the estimating unit 181. That is to say, in the above-mentioned embodiment, element values of the eigenvector "Ve" of the element covariance matrix are used as reception correction values for correcting the reception wavefront distortion and element values of the eigenvector "Vt" of the element covariance matrix are used as transmission correction values for correcting the transmission wavefront distortion. The correction values that are used for the correction processing are, however, not limited to the eigenvector itself. A main component causing disturbance of an image due to the wavefront distortion is phase. In consideration of this, setting of "phases of eigenvector element values" as "correction value phases (phase values for correction)" can also provide a correction effect of the wavefront distortion sufficiently.

To be specific, the correction unit 182 may use a unit vector having, as elements, "complex numbers with phases" that are elements of the eigenvector as correction values that are used for the correction processing based on the wavefront distortion estimated by the estimating unit 181.

For example, "Ve=[ve1, ..., vem, ..., veM]" is the eigenvector "Ve" derived by the estimating unit 181. In this case, the correction unit 182 calculates a correction value (reception correction value) by the following equation (7). Note that "m" as indicated in the equation (7) satisfies "1≤m≤M, m is an integer".

$$vem/(|vem|\sqrt{M}) \quad (7)$$

The equation (7) indicates that a vector divided by the "square root of M" is calculated because each element has the same phase as an eigenvector element and norm of the vector is "1". The correction unit 182 calculates a correction value (transmission correction value) by the same processing as the above-mentioned processing also when the eigenvector "Vt" is output from the estimating unit 181. Also in the modification, the wavefront distortion can be corrected with higher accuracy.

The ultrasonic imaging method as described in the above-mentioned embodiment and modifications may be executed by a signal processing device installed independent of the ultrasonic diagnostic device and having the functions of the above-mentioned signal processor 18, controller 19, and the like, the signal processing device acquiring the reception signal groups from the receiver 12.

Furthermore, all of or a part of processing that have been described to be performed automatically among the pieces of processing as described in the above embodiments can be performed manually. Alternatively, all of or a part of processing that have been described to be performed manually among the pieces of processing as described in the above embodiment can be performed automatically by a known method. In addition, information including processing procedures, control procedures, specific names, and various pieces of data and parameters as described in the above-described document and drawings can be changed in any manner unless otherwise specified.

The constituent components of the devices as illustrated in the drawings are conceptual functionally and are not necessarily required to be configured as illustrated in the drawings physically. That is to say, specific forms of disintegration and integration of the devices are not limited to those as illustrated in the drawings, and all of or a part of them can be configured to be disintegrated or integrated functionally or physically based on any unit depending on various loads and usage conditions. Furthermore, all of or a part of the pieces of processing that are performed by the devices can be executed by a central processing unit (CPU) and a computer program that is analyzed and executed by the CPU or can be executed as hardware by a wired logic.

The ultrasonic imaging method as described in the above-mentioned embodiment and modifications may be executed by executing an ultrasonic imaging program prepared in advance by a computer such as a personal computer and a workstation. The ultrasonic imaging method can be distributed through a network such as the Internet. Furthermore, the ultrasonic imaging method can be also executed by being recorded in a computer readable recording medium such as a hard disk, a flexible disk (FD), a compact disc read only memory (CD-ROM), a magnetooptic disc (MO), and a digital versatile disc (DVD) and being read from the recording medium by the computer.

The pieces of processing by the respective constituent components as described in the above-mentioned embodiment and modifications can be executed as a correction method that can be executed by a computer such as a personal computer and a workstation. For example, the computer acquires a plurality of complex images corresponding to respective deflection angles from reception signal groups based on reflection waves received by respective elements included in an ultrasonic probe by plane waves transmitted at the respective deflection angles from the ultrasonic probe including the elements and estimates wavefront distortion at the time of transmission using the complex pixel values of the acquired complex images. Then, the computer performs the correction processing based on the wavefront distortion at the time of transmission on the reception signal groups so as to generate image data based on the complex pixel values of the complex images for the respective deflection angles that are acquired from the reception signal groups after the correction processing.

Other Configurations

Figure 10:
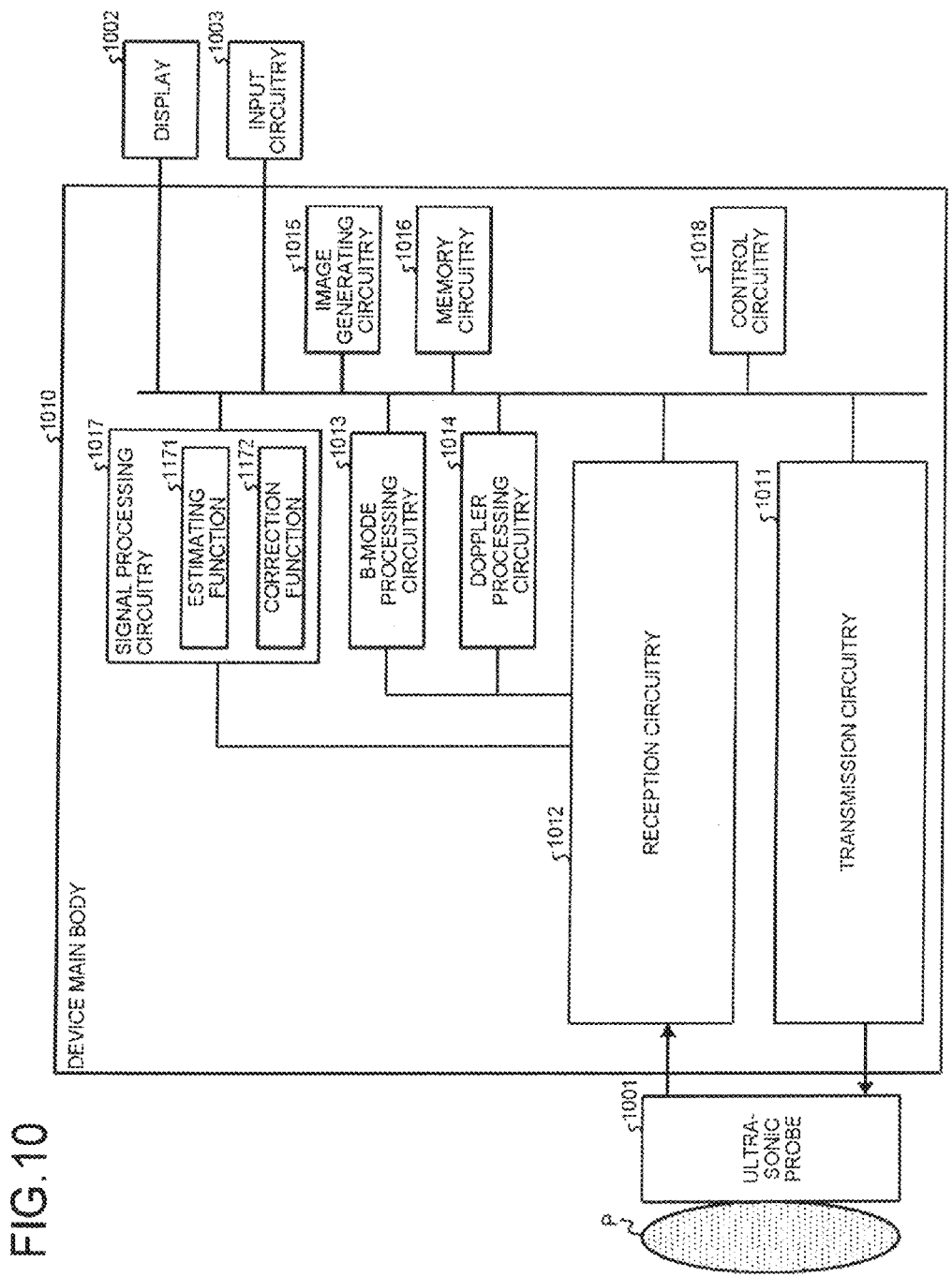
FIG. 10 is a block diagram illustrating an example of the configuration of an ultrasonic diagnostic device according to other embodiments.

For example, the ultrasonic diagnostic device shown in FIG. 1 may be configured as shown in FIG. 10. FIG. 10 is a block diagram illustrating an example of the configuration of an ultrasonic diagnostic device according to other embodiments.

As illustrated in FIG. 10, an ultrasonic diagnostic device includes an ultrasonic probe 1001, a display 1002, input circuitry 1003, and a device main body 1010. The ultrasonic probe 1001, the display 1002, the input circuitry 1003, and the device main body 1010 correspond to the ultrasonic probe 1, the monitor 2, the input unit 3, and the device main body 10 shown in FIG. 1, respectively.

The device main body 1010 includes transmission circuitry 1011, reception circuitry 1012, B-mode processing circuitry 1013, Doppler processing circuitry 1014, image generating circuitry 1015, memory circuitry 1016, signal processing circuitry 1017, and control circuitry 1018. The transmission circuitry 1011, the reception circuitry 1012, the B-mode processing circuitry 1013, the Doppler processing circuitry 1014, the image generating circuitry 1015, the signal processing circuitry 1017, and the control circuitry 1018 correspond to the transmitter 11, the receiver 12, the B-mode processor 13, the Doppler processor 14, the image generator 15, the signal processor 18, and the controller 19 shown in FIG. 1, respectively. The memory circuitry 1016 correspond to the image memory 16 and the internal storage unit 17 shown in FIG. 1. The transmission circuitry 1011 is an example of transmission circuitry in the accompanying claims. The reception circuitry 1012 is an example of reception circuitry in the accompanying claims. The signal processing circuitry 1017 is an example of signal processing circuitry in the accompanying claims. The control circuitry 1018 is an example of control circuitry in the accompanying claims.

The signal processing circuitry 1017 performs an estimating function 1171 and a correction function 1172. The estimating function 1171 is a function implemented by the estimating unit 181 illustrated in FIG. 1. The correction function 1172 is a function implemented by the correction unit 182 illustrated in FIG. 1.

For example, each of the respective processing functions performed by the estimating function 1171 and the correction function 1172 which are components of the signal processing circuitry 1017 illustrated in FIG. 10, is stored in the memory circuitry 1016 in a form of a computer-executable program. The signal processing circuitry 1017 is a processor that loads programs from the memory circuitry 1016 and executes the programs so as to implement the respective functions corresponding to the programs. In other words, the signal processing circuitry 1017 that has loaded the programs has the functions illustrated in the signal processing circuitry 1017 in FIG. 10. That is, the signal processing circuitry 1017 loads a program corresponding to the estimating function 1171 from the memory circuitry 1016 and executes the program so as to perform the same processing as that of the estimating unit 181. The signal processing circuitry 1017 loads a program corresponding to the correction function 1172 from the memory circuitry 1016 and executes the program so as to perform the same processing as that of the correction unit 182.

FIG. 11 is a flowchart of a processing procedure of the ultrasonic diagnostic device according to other embodiments. As shown in FIG. 11, the transmission circuitry 1011 causes an ultrasonic probe 1 including a plurality of elements to transmit plane waves at a plurality of different deflection angles (step S101). The reception circuitry 1012 generates reception signal groups based on reflection waves that the individual elements included in the ultrasonic probe 1 receive in response to the transmission of the plane waves at the different deflection angles (step S102). The signal processing circuitry 1017 acquires a plurality of complex images corresponding to the respective deflection angles from the reception signal groups and estimates wavefront distortion at the time of transmission using the complex pixel values of the complex images (step S103). The signal processing circuitry 1017 perform correction processing based on the wavefront distortion at the time of transmission on the reception signal groups so as to generate image data based on the complex pixel values of the complex images for the respective deflection angles that are acquired from the reception signal groups after the correction processing (step S104). The control circuitry 1018 causes a display to display 1002 the image data after the correction processing by the signal processing circuitry (step S105).

For example, Steps S103 illustrated in FIG. 11 is a step that is implemented by the signal processing circuitry 1017 loading the program corresponding to the estimating function 1171 from the memory circuitry 1016 and executing the program. Step S104 illustrated in FIG. 11 is a step that is implemented by the signal processing circuitry 1017 loading the program corresponding to the correction function 1172 from the memory circuitry 1016 and executing the program.

In FIG. 10, the processing functions performed by the estimating function 1171 and the correction function 1172 are described as being implemented in the single processing circuit (signal processing circuitry). The functions, however, may be implemented by configuring a processing circuit by combining a plurality of separate processors and causing each of the processors to execute a program.

The term "processor" used in the above description means, for example, a central preprocess unit (CPU) and a graphics processing unit (GPU), or a circuit such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in a storage circuit. Instead of being stored in a storage circuit, the program may be built directly in a circuit of the processor. In this case, the processor implements a function by loading and executing the program built in the circuit. The processors in the present embodiment are not limited to a case in which each of the processors is configured as a single circuit. A plurality of separate circuits may be combined as one processor that implements the respective functions. Furthermore, the components illustrated in FIG. 10 may be integrated into one processor that implements the respective functions.

The respective circuitry exemplified in FIG. 10 may be distributed or integrated as appropriate. For example, the signal processing circuitry 1017 and the control circuitry 1018 may be integrated.

As described above, the above-mentioned embodiment and modifications enable the wavefront distortion to be corrected more accurately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic device, comprising:
   transmission circuitry configured to cause an ultrasonic probe including a plurality of transducer elements to transmit plane waves at a plurality of different deflection angles;
   reception circuitry configured to generate reception signal groups based on reflection waves received by an individual transducer element included in the ultrasonic probe, the reflection waves being generated by transmission of the plane waves at the respective deflection angles;
   signal processing circuitry configured to
      acquire a plurality of complex images corresponding to the respective deflection angles from the reception signal groups and estimate wavefront distortion at the time of transmission using complex pixel values of the complex images, the wavefront distortion being a variation in a wavefront of the plane waves due to a non-uniform layer of a subject, and
      perform correction processing based on the wavefront distortion at the time of transmission by multiplying the reception signal groups by an eigenvector corresponding to a maximum eigenvalue of a pixel-wise covariance matrix obtained from the reception signal groups corresponding to each of the deflection angles so as to generate image data based on the complex pixel values of the complex images for the respective deflection angles that are acquired from the reception signal groups after the correction processing; and
   control circuitry configured to cause a display to display the image data after the correction processing by the signal processing circuitry.

2. The ultrasonic diagnostic device according to claim 1, wherein
   the signal processing circuitry is further configured to
      estimate the wavefront distortion at the time of reception using the reception signal groups, and
      perform correction processing using the wavefront distortion at the time of reception by multiplying the reception signal groups by an eigenvector corresponding to a maximum eigenvalue of a transducer-element-wise covariance matrix obtained from the reception signal groups corresponding to each of the deflection angles, and
   the control circuitry is further configured to control the signal processing circuitry so as to repeat estimation processing of the wavefront distortion at the time of transmission and the correction processing based on the wavefront distortion at the time of transmission, and estimation processing of the wavefront distortion at the time of reception and the correction processing based on the wavefront distortion at the time of reception a plurality of times.

3. The ultrasonic diagnostic device according to claim 2, wherein the signal processing circuitry is further configured to perform the estimation processing of the wavefront distortion at the time of reception by calculating the an eigenvector corresponding to the a maximum eigenvalue of a the transducer-element-wise covariance matrix.

4. The ultrasonic diagnostic device according to claim 2, wherein the signal processing circuitry is further configured to
   divide a video image formation region into a plurality of first image regions, the video image formation region being a region on which a video image is formed by the transmission of the plane waves,
   perform estimation processing to estimate the wavefront distortion at the time of reception on a plurality of second image regions corresponding to the first image regions in the complex images, and
   perform the correction processing based on the estimated wavefront distortion on each of the second image regions.

5. The ultrasonic diagnostic device according to claim 4, wherein the first image regions are regions formed by dividing the video image formation region into the plurality of first regions in at least one direction of an azimuth direction and a depth direction.

6. The ultrasonic diagnostic device according to claim 4, wherein the first image regions are formed by division with a pattern that is different between estimation processing of the wavefront distortion at the time of transmission and estimation processing of the wavefront distortion at the time of reception.

7. The ultrasonic diagnostic device according to claim 1, wherein the signal processing circuitry is further configured to perform the estimation processing of the wavefront distortion at the time of transmission by calculating the an eigenvector corresponding to a the maximum eigenvalue of a the pixel-wise covariance matrix.

8. The ultrasonic diagnostic device according to claim 7, wherein
   the reception signal groups are complex signal groups formed by converting signals based on the reflection waves received by individual transducer elements included in the ultrasonic probe by quadrature detection or Hilbert transformation, and
   the signal processing circuitry is further configured to provide a delay to each of the complex signal groups for focusing on each pixel on an image so as to calculate a complex signal sequence for reconstructing each pixel, calculate a the pixel-wise covariance matrix using each complex signal sequence, and calculate the an eigenvector corresponding to the a maximum eigenvalue of the pixel-wise covariance matrix of each pixel or an another eigenvector corresponding to a maximum eigenvalue of a matrix formed by cumulating or averaging covariance matrices of a plurality of pixels.

9. The ultrasonic diagnostic device according to claim 8, wherein the signal processing circuitry is further configured to use the eigenvector corresponding to the maximum eigenvalue of the pixel-wise covariance matrix or a unit vector having, as an element, a complex number with a phase as an element of the eigenvector as a correction value that is used for the correction processing based on the estimated wavefront distortion at the time of transmission estimated.

10. The ultrasonic diagnostic device according to claim 1, wherein the signal processing circuitry is further configured to
divide a video image formation region into a plurality of first image regions, the video image formation region being a region on which a video image is formed by the transmission of the plane waves,
perform estimation processing to estimate the wavefront distortion at the time of transmission on a plurality of second image regions corresponding to the first image regions in the complex images, and
perform the correction processing based on the estimated wavefront distortion on each of the second image regions.

11. The ultrasonic diagnostic device according to claim 10, wherein the first image regions are regions formed by dividing the video image formation region into the plurality of first regions in at least one direction of an azimuth direction and a depth direction.

12. The ultrasonic diagnostic device according to claim 10, wherein when the video image formation region is discretely divided and the first image regions are set, the signal processing circuitry is further configured to derive wavefront distortion on regions other than the first image regions by spatial interpolation processing using the wavefront distortion estimated on each of the first image regions.

13. The ultrasonic diagnostic device according to claim 1, wherein when generation of the image data by the transmission of the plane waves using the deflection angles is performed over a plurality of frames, the signal processing circuitry is configured to use wavefront distortion estimated in generating a first frame among the frames of image data so as to perform the correction processing to output a second frame subsequent to the first frame.

14. The ultrasonic diagnostic device according to claim 1, wherein the signal processing circuitry is further configured to estimate the wavefront distortion at the time of transmission, a phase difference from an ideal reception wavefront at each transducer element, or a difference in rate of propagation of the reception wavefront.

15. The ultrasonic diagnostic device according to claim 1, wherein the signal processing circuitry is further configured to perform the correction processing when a degree of the estimated wavefront distortion at the time of transmission exceeds a threshold.

16. The ultrasonic diagnostic device according to claim 1, wherein the signal processing circuitry is configured to perform estimation processing and correction processing to estimate and correct wavefront distortion at the time of transmission on a region specified as a region for providing the image data in a region that is scanned by transmission of plane waves at the deflection angles.

17. The ultrasonic diagnostic device according to claim 1, wherein the signal processing circuitry is further configured to generate non-corrected image data using a reception signal obtained through the transmission of the plane waves without performing the correction processing, and the control circuitry is configured to cause the display to display the image data and the non-corrected image data simultaneously or in a switching manner.

18. The ultrasonic diagnostic device according to claim 1, wherein the signal processing circuitry is further configured to
estimate the wavefront distortion at the time of transmission using complex pixel values of pixels with which sources of reflection are provided at a same position in each of the complex images, and
generate image data based on the complex pixel values of pixels with which the sources of reflection are provided at the same position in each of the complex images for the respective deflection angles that are acquired from the reception signal groups after the correction processing.

19. A correction method, comprising:
acquiring a plurality of complex images corresponding to a plurality of different deflection angles from reception signal groups based on reflection waves received by an individual transducer element of a plurality of transducer elements included in an ultrasonic probe by plane waves transmitted at the respective deflection angles from the ultrasonic probe including the transducer elements, and estimating wavefront distortion at the time of transmission using complex pixel values of the complex images, the wavefront distortion being a variation in a wavefront of the plane waves due to a non-uniform layer of a subject, and
performing correction processing based on the wavefront distortion at the time of transmission by multiplying the reception signal groups by an eigenvector corresponding to a maximum eigenvalue of a pixel-wise covariance matrix obtained from the reception signal groups corresponding to each of the deflection angles so as to generate image data based on the complex pixel values of the complex images for the respective deflection angles that are acquired from the reception signal groups after the correction processing.

* * * * *